US006719964B1

(12) United States Patent
Shapiro et al.

(10) Patent No.: US 6,719,964 B1
(45) Date of Patent: Apr. 13, 2004

(54) COMPOSITIONS FOR PREVENTION OF CHEMICALLY INDUCED IRRITATION AND DISCOLORATIONS AND METHODS OF USING SAME

(75) Inventors: Warren Shapiro, Loveland, OH (US); Jon Anderson, Galesburg, MI (US)

(73) Assignee: Premier Specialties Inc., Middlesex, NJ (US)

( * ) Notice: Subject to any disclaimer, the term of this patent is extended or adjusted under 35 U.S.C. 154(b) by 0 days.

(21) Appl. No.: 09/900,652

(22) Filed: Jul. 7, 2001

(51) Int. Cl.[7] ............................. A61K 7/44; A61K 7/42
(52) U.S. Cl. ........................................... 424/60; 424/59
(58) Field of Search ...................................... 424/59, 60

(56) References Cited

U.S. PATENT DOCUMENTS

| 4,136,165 | A | * | 1/1979 | Moller et al. ................. 424/60 |
| 4,981,845 | A | * | 1/1991 | Pereira ........................ 514/557 |
| 5,770,183 | A | * | 6/1998 | Linares ........................ 424/59 |
| 6,043,204 | A | * | 3/2000 | Kaufman et al. ............. 424/59 |

* cited by examiner

*Primary Examiner*—Herbert J. Lilling
(74) *Attorney, Agent, or Firm*—Peter B. Scull, Esq.; Dahl & Osterloth, LLP

(57) ABSTRACT

A new and improved cosmetic composition and method of using the same to prevent and treat chemically induced skin irritation and discoloration and protect from the adverse effects of tyrosinase containing a small but effective amount of ethyl p-methoxycinnamate derived from Kaempferia Galanga roots.

10 Claims, No Drawings

COMPOSITIONS FOR PREVENTION OF CHEMICALLY INDUCED IRRITATION AND DISCOLORATIONS AND METHODS OF USING SAME

INTRODUCTION

The present invention relates generally to novel and unique body preparations and method of making and using the same, and more particularly to a new and improved lotion containing a small but effective amount of ethyl p-methoxycinnamate specifically obtained from Kaempferia Galanga Root Extract in a cosmetically and pharmacologically acceptable carrier. The preparation is found to prevent and treat chemically induced skin irritations and discoloration caused by many of the currently marketed skin-care products.

BACKGROUND OF THE INVENTION

A number of botanically derived substances have been heretofore employed from time-to-time in a variety of body lotions. Typical of such substances are arbuten, kojic acid, mulberry and ascorbic acid. However, none of these substances were capable of inhibiting chemically induced irritation in spite of their alleged ability to inhibit the formation of tyrosine. U.S. Pat. No. 4,136,165 claims the use of alkyloxybenzoic esters including ethyl p-methoxycinnamate to protect human skin against inflammation resulting from sunburn. Its use comprised topically applying to the skin a layer of the composition sufficient to inhibit inflammation from sunburn. The body of the patent describes the use of these compounds in cosmetic preparations, particularly for protection against sunburn and for the treatment of sunburn. It further describes anti-inflammatory activity measured by the rat's paw test that shows the effect of oral administration of the test compounds on the swelling of the rat's paw following injection into the paw of a known irritant. There is also data showing the protection from UV induced edema in the hairless mouse and guinea pig. However, there is no teaching nor even a hint for the inhibition of tyrosinase or of a topical anti-inflammatory effect for erythema caused by agents other than UV radiation in the above mentioned patent. Ultraviolet Absorbing Skin Cosmetic (Japanese patent JP 8157346) describes a UV absorbing skin cosmetic containing extracts of one or more plants selected from Kaempferia Galanga. The skin cosmetic absorbs the UV light in the UV-A region and/or the UV-B region. This patent does not however mention inhibition of tyrosinase or chemically induced irritation. Another patent, Zihuasong Freckle-Eliminating Face Cream and its Compounding Process, Chinese patent CN 1166359, describes a face cream containing over twenty Chinese medicinal materials including Kaempferia Galanga that is capable of improving the nutritive state of skin and promote the metabolism of skin cells. The disclosed facial cream has an obvious curative effect on chloasma, pregnancy plaque, senile plaque and freckles but does not mention the inhibition of tyrosinase or inhibition of chemical irritation. Another Chinese patent (CN 1149452) Spot-Removing Cream Made From Multiple Chinese Herbal Medicines, describe a cosmetic cream composed of mung bean 32–25% and eight other botanicals, including Kaempferia Galanga, in a paste to remove spots on the face and also moisten and whiten the skin. There is again no mention of inhibition of tyrosinase or chemical irritation. Multi-Function Monosaccharides Medicinal Composition (Chinese patent CN 1256944) describes a preparation including nineteen Chinese medicinal materials (including galanga root) that can be used for curing various skin diseases. Once again there is no mention of inhibition of tyrosinase or chemical irritation. The Chinese patent (CN1100300) Hair Oil describes the use of a preparation prepared from Kaempferia Galanga and other botanicals for hair care and curing alopecia. There is no mention of tyrosinase or chemical irritation. The Isolation of Ethyl p-methoxycinnamate, the major antifungal principle of Curcumba zedoaria, by Gupta et al, Lloydia 1976 Jul.–Aug. ; 39(4): 218–22. The other inventions are confined to use of methoxycinnamates as UV sunscreens or the use of mixtures of a number of botanicals to address removal of spots or freckles. None of the patents mention the mechanisms of inhibition of tyrosinase of relief of chemical irritation. The other inventions are confined to use of methoxycinnamates as UV sunscreens or the use of mixtures of a number of botanicals to address removal of spots or freckles. None of the patents mention the inhibition of tyrosinase as the relief of chemical irritation.

BRIEF SUMMARY OF THE INVENTION

The present invention is directed making and utilizing a therapeutic composition containing up to about 5.0 weight percent, preferably from about 0.1 to about 1.0 weight percent of ethyl p-methoxycinnamate extracted from Kaempferia Galanga root. It should be noted that from about 0.1 to 1.0 weight percent of root extract is adequate for most applications. The composition is prepared by incorporating the root extract into a cosmetically or pharmaceutically acceptable carrier and thereafter used to prevent and treat chemically induced skin irritation such as erythema, stinging, burning which can be caused by the use of chemical irritants such as hydroxy acids and the like, and prevent and treat skin discolorations resulting from chemically induced irritation and post inflammatory hyperpigmentation by inhibiting the formation of tyrosinase. Incorporation of the Kaempferia Galanga root extract into a skin care regimen of products may allow consumers with sensitive skin to use products to cleanse, moisturize, tone and reverse the signs of aging, that they could otherwise not use for fear of unwanted skin reactions. Furthermore, the Kaempferia Galanga root extract imparts a natural, pleasant odor that can cover the off-odors of many cosmetic/pharmaceutical formulations without the necessity of using a fragrance compound. This is another advantage for consumers that have sensitive skin reactions to fragrance as well as other ingredients used in conventional skin care products.

DESCRIPTION OF THE PREFERRED EMBODIMENT

The present invention relates to the use of ethyl p-methoxycinnamate which has been extracted from Kaempferia Galanga root by placing the root in an alcohol bath, heating in the alcohol bath to extract the cinnamate from the root; separating the alcohol solution from the root residue, and thereafter heating the alcohol extract for a time sufficient to evaporate substantially all of the alcohol therefrom. The residue using conventional assay techniques, which need not be disclosed here, consists essentially of highly purified ethyl p-methoxycinnamate. This compound is then used to prepare topical cosmetic preparations containing up to about 5% by weight of the root extract, preferably from about 0.1% (w/w) up to about 1.0% (w/w), which is thoroughly blended into a conventional cosmetic base as will be hereafter described in detail. It is to be noted that for most of the conditions targeted root extract in the amount of 0.1 to 1.0 percent by weight is sufficient to achieve the desired results.

In formulating the ultimate composition, a number of traditional ingredients may be used. For instance, water; lanolin; Vaseline; glycerol; triglycerides of fatty acids; polyethylene glycols; oxyethyleneated fatty alcohols; esters such as isopropyl palmitate; myristate and stearate; silicone oils; oleyl oleate and butyl stearate; animal, vegetable, or mineral oils; fatty alcohols; glycerol monostearate, and organic and mineral waxes. These ingredients are generally used in an amount of about 10% to 97% by weight of the total formulation and can be either a single or a multiple phase system.

Other cosmetic ingredients which may also be used in the composition of the present invention include: thickeners, softeners, superfatting agents, emollients, wetting agents and surface active agents, as well as preservatives, anti-foam agents, perfumes or any other compatible ingredient usually employed in cosmetics.

Among the solvents which may be used are water, lower monoalcohols as well as their mixtures, or aqueous-alcoholic or oil/alcoholic solutions. The alcohols preferably used being ethanol, isopropyl alcohol, propylene glycol, glycerol and sorbitol, and the aqueous-alcoholic mixtures used preferably being mixtures of water and ethyl alcohol.

For topical application, the compositions must be non-toxic and non-irritating to the skin tissue and capable of application to the skin as a uniform continuous film. In addition, the active agents must be chemically stable and in particular must be resistant to chemical and photodegradation when on the skin.

In one practice of the present invention, a suitably sized water-jacketed stainless steel tank, useful for both heating and cooling, is charged with Phase 1 mixture and the propeller agitation is activated. Phase I and II are then mixed at about 80° C. after the Phase 2 mixture is added and stirred, the Phase III ingredients are blended in. Then the tank is cooled to 50° C. or lower, and the Phase IV ingredients are added and the mixture is stirred until it is substantially uniform and all ingredients are homogeneously dispersed at about 35° C. Where additional Phases are added after Phase IV, the stirring will be conducted at a temperature of 50° C. until blended and then cooled to 35° C.

As indicated, the composition hereof is prepared in distinct phases which are thereafter and sequentially blended into a simple homogeneous mixture for ultimate use. The temperature of the tank is controlled by regulating the temperature of the water passing through the jacket using conventional technology.

It has been found preferable to limit the amount of root extract to about 0.2 weight percent when the intended area of use is on or near the eyes, to about 0.5 weight percent for other portions of the face and from about 0.75 to about 1.0% when the target area is hands, arms, legs, and other portions of the body. A typical composition of each is shown in the following examples.

Using the foregoing procedure, compositions embodying the present invention were prepared from the ingredients shown below. The ingredients other than the root extract are shown as illustrative and any of the well known equivalents may be substituted therein.

EXAMPLE I

A typical hand cream is prepared using the mixing technique described above with the following phases. Phase I, using a weight percent based on the final mixture contains: water (water), q.s.; Butylene Glycol (Butylene Glycol) 5.00%; Glycerin 99% (Glycerin) 5.00%; Hampene Na2 (Disodium EDTA) 0.10%; and TEA 99 (Triethanolamine) 0.25%.

Phase II consists of: Panalene L14(Hydrogenated Polyisobutane) 7.00% ; Finsolv TN (C12–15 Alcohols Benzoate) 3.00%; Stearic Acid (Stearic Acid) 2.00%; Lipo GMS 450 (Glyceryl Stearate SE) 3.00%; Brookswax D (Cetearyl Alcohol & Ceteareth-20) 2.00%; Cetyl (Cetyl Alcohol) 1.00; California Grapeseed Oil (Grapeseed Oil) 1.25% ; Vitamin E Acetate (Tocopheryl Acetate) 0.50% ; RitaCeti (Cetyl Esters) 1.75%; DC 200 Fluid 100 cst. (Dimethicone)1.20%; and Kaempferia Galanga Root Extract 0.75%.

Phase III consists of: Water (Water) 2.00%; and TEA 99 (Triethanolamine) 0.25%.

Phase IV consist of PHENONIP (Phenoxyethanol & Methylparaben & Ethylparaben & Butylparaben & Propylparaben) 1.00%.

EXAMPLE II

A typical facial cream, using the technique of Example I, is prepared by using the following phase composition. Phase I consists of. Water (Water) q.s. ; KELTROL (Xanthan Gum) 0.10% ; and VEEGUM (Magnesium Aluminum Silicate) 20%.

Phase II consists of PANALENE L14(Hydrogenated Polyisobutane) 1.25%; FINSOLV TN (C12–15 Alcohols Benzoate) 2.00%; Stearic Acid (Stearic Acid) 1.75%; RITA GMS (Glycerol Stearate) 2.70%; BROOKSWAX D (Cetearyl Alcohol & Ceteareth-20) 1.00%; California Grapeseed Oil (Grapeseed Oil) 1.00%; Vitamin E Acetate (Tocopheryl Acetate) 0.25%; Shebu (Shea Butter) 0.75%; Mango Butter (Mango Butter) 0.75%; 345 FLUID (Cyclomethicone) 1.00%; Cetyl Alcohol (Cetyl Alcohol) 1.25%; 200 FLUID 350CST (Dimethicone) 0.70%; and Kaempferia Galanga Root Extract 0.20%.

Phase III consist of: Water (Water) 2.00%; and TEA 99 (Triethanolamine) 0.55%.

Phase IV consists of Germaben II (Propylene Glycol & Diazolidinyl Urea & Methylparaben & Propylparaben) 1.00%.

EXAMPLE III

Using the same procedures as described in Example I and II, a representative eye cream is prepared using the following phase composition: Phase I consists of Water (Water) q.s.; and ULTREZ 10 (Carbomer) 0.10%.

Phase II consists of: FINSOLV TN (C12–15 Alkyl Benzoate) 2.00%; Stearic Acid (Stearic Acid) 1.50%; RITA GMS (Glyceryl Stearate) 1.50%; Jojoba Oil (Jojoba Oil) 2.00%; Cetyl Alcohol (Cetyl Alcohol) 1.70%; RITACETI (Cetyl Esters) 1.00%; 345 FLUID (Cyclomethicone) 1.50%; 200 FLUID 100CST (Dimethicone) 1.00%; and Kaempferia Galanga Root Extract 0.20%.

Phase III consists of: Water (Water) 2.00%; and TEA 99 (Triethanolamine) 0.48%.

Phase IV consists of Water (Water) 5.00%; Butylene Glycol (Butylene Glycol) 5.00%; Glycerin (Glycerin) 3.00%; and DC193 (Dimethicone Copolyol) 1.00%.

Phase V consists of: GERMABEN II (Propylene Glycol & Diazolidinyl Urea & Methylparaben & Propylparaben.

Phase VI consists of: SEPIGEL 305 (Polyacrylamide & C13–14 Isoparaffin & Laureth-7) 1.00%.

EXAMPLE IV

The following tests were conducted to demonstrate the tyrosinase inhibiting properties of Kaempferia Galanga Root Extract. The test is based on the known fact that active Tyrosinase catalyzes the oxidation of L-tyrosine to L-DOPA and L-DOPA to dopaquinone. These reactions are the initial steps of melanin biosynthetic pathways. Tyrosinase has heretofore been used as the target enzyme for the inhibition of melanin biosynthesis in the process of searching for anti-hyperpigmentating agents. A simple assay method is established to test the tyrosinase inhibition effects of the test compounds. The assay uses L-tyrosine as substrate to examine the tyrosinase activity by the dopachrome in the presence or absence of test compounds. The reaction mixture contains 0.55 mM L-tyrosine in 10 mM phosphate buffer pH 6.8 in the presence or absence of testing compound at various concentrations. Thirty units of mushroom tyrosinase are added to initiate the reaction. The absorbance of the reaction mixture is measured at 475 nm after 10 minutes incubation at 37° C.

Tyrosinase activity kinetics curve was determined with scanning at 475 nm for time 0 minutes to 15 minutes. The result showed that the tyrosinase was in good quality. The tyrosinase activity was observed with measurable ranges (Table 1). The same amount of tyrosinase was used in the assay of Kaempferia Galanga Root Extract at 0.2%, 0.1%, 0.05%, 0.01%, 0.005% and 0.001% with water as blank without tyrosinase and with tyrosinase only as a positive control. The kaempferia Galanga Root Extract inhibited tyrosinase activity in all testing concentrations in dose dependence manner as shown in Table 2.

TABLE 1

Tyrosinase Activity

| Time (secs) | Absorption |
| --- | --- |
| 0 | 0.09 |
| 100 | 0.12 |
| 200 | 0.2 |
| 300 | 0.3 |
| 400 | 0.4 |
| 500 | 0.5 |
| 600 | 0.6 |
| 700 | 0.65 |
| 800 | 0.7 |
| 900 | 0.75 |

TABLE 2

Percentage of inhibition of tyrosinase activity with the treatment of Kaempferia Galanga Root Extract

| Treatment & Concentration | Percent of Inhibition (approx.) |
| --- | --- |
| 0.2% Galanga Extract | 50% |
| 0.1% Galanga Extract | 45% |
| 0.05% Galanga Extract | 39% |
| 0.01% Galanga Extract | 37% |
| 0.005% Galanga Extract | 19% |

EXAMPLE V

The below described method was used to demonstrate the inhibition of chemically induced erythema by Kaempferia Galanga Root Extract.

Nine human subjects who met specific inclusion criteria were selected for participation to determine a test product's ability to reduce erythema caused by application of a known chemical irritant (15% lactic acid).

Erythema was measured utilizing a MINOLTA CHROMA Meter CR-300. The $a^*$ value of the $L^* a^* b^*$ color notation system is indicative of color changes in the red-green color axis.

The higher the $a^*$ value, the more intensely red the object being evaluated. Therefore, the $a^*$ value is used as a measure of redness (erythema) on the skin surface, where an increase in value indicates an increase an increase in erythema. A decrease in the $a^*$ value represents a reduction in "redness" of the skin and is considered to be evidence of reduced erythema.

Seven 1"×1.5" test site areas were outlined with a surgical marking pen on each subject's forearm. These areas were designated for the Test Materials and an untreated chemically insulted control.

A 0.2 ml of the 15% lactic acid solution was applied to the ¾"×3/4" gauze portion of an adhesive dressing, to induce an erythemal response. These were then applied to the appropriate treatment sites to form occluded patches. These patches were removed after four hours. The subjects sat for approximately thirty minutes before evaluations allowing any irritation from the patches to subside.

The site were evaluated by the following scoring system:

0=Negative, no visible reaction
0.5=Minimal erythema
1.0=Defined erythema
2.0=Moderate erythema
3.0=Severe erythema When a test site achieved a visual assessment score of at least 0.5 (minimal erythema) but no greater than 2.0 (moderate erythema), MINOLTA CHROMA Meter base readings were taken. 0.2 ml of the Test Material was applied to the appropriate chemically insulted site, with the remaining chemically insulted site as the untreated control.

Approximately 30 minutes, 1 hour, and 4 hours after the Test Material was applied to the appropriate chemically insulted sites, erythema/irritation responses were evaluated for all sites, both visually and by use of the MINOLTA CHROMA Meter.

The subjects returned to the clinic approximately 24 hours after the test sites were treated with the Test Material, and a final visual evaluation and MINOLTA CHROMA Meter readings were taken.

The inhibition of chemically induced erythema by Kaempferia Galanga Root Extract at 1.0% and 0.5% is shown in Table 3. The results for 1.0% were statistically significant at 4 hours and 24 hours. The results for 0.5% showed some improvement but were not statistically significant.

TABLE 3

Kaempferia Galanga Root Extract
Reduction of lactic acid induced Erythema

| Time (hr) | 1% Galanga | 0.5% Galanga |
| --- | --- | --- |
| 0.5 | −5% | 0% |
| 1 | 6% | 1% |
| 4 | 14% | 11% |
| 24 | 21% | 14% |

From the foregoing, it is apparent that an invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended here.

Accordingly, what is claimed is:

1. A method of protecting mammalian skin from the harmful effects of tyrosinase and chemically induced irritation other than UV radiation comprising applying to skin in need thereof a preparation containing, in weight percent, an effective amount up to about 5 percent of ethyl p-methoxycinnamate dispersed in a nontoxic, nonirritating cosmetically acceptable carrier.

2. A method of protecting mammalian skin according to claim 1 in which said carrier is an emulsion.

3. A method of protecting mammalian skin according to claim 1 in which said carrier is an anhydrous solvent.

4. A method of protecting mammalian skin according to claim 1 in which said carrier is a single phase system.

5. A method according to claim 1 containing from about 0.1% up to about 5.0% of ethyl p-methoxycinnamate (wt/wt).

6. A method of protecting mammalian skin according to claim 5 in which said carrier is an emulsion.

7. A method of protecting mammalian skin according to claim 5 in which said carrier is an anhydrous solvent.

8. A method of protecting mammalian skin according to claim 5 in which said carrier is a single phase system.

9. A method according to claim 1 in which said ethyl p-methoxycinnamate is extracted from Kaempferia Galanga root.

10. A method according to claim 5 in which said ethyl p-methoxycinnamate is extracted from Kaempferia Galanga root.

* * * * *